United States Patent [19]

Beaton et al.

[11] Patent Number: 5,625,050
[45] Date of Patent: Apr. 29, 1997

[54] MODIFIED OLIGONUCLEOTIDES AND INTERMEDIATES USEFUL IN NUCLEIC ACID THERAPEUTICS

[75] Inventors: Graham Beaton; Eric F. Fisher, both of Boulder, Colo.

[73] Assignee: Amgen Inc., Thousand Oaks, Calif.

[21] Appl. No.: 221,425

[22] Filed: Mar. 31, 1994

[51] Int. Cl.$^6$ .................................................. C07H 21/04
[52] U.S. Cl. .................................................. 536/24.1
[58] Field of Search .................................. 536/24.1, 25.3, 536/23.1

[56] References Cited

PUBLICATIONS

Heinemann et al., Nucleic Acids Research (1991), vol. 19 (3): pp. 427–433.
Mazur et al., Tetrahedron (1984), vol. 40 (20): pp. 3949–3956.
Crockett, Aldrichimica (1983), vol. 16 (3): pp. 47–56.
Morr et al., GBF Monogr. Ser., 8(Chem. Synth. Mol. Biol.) 1987, pp. 107–113.
Bjergarde et al., Nucleic Acids Research 19, 1991, 5843–5850.
Worms et al, in. Organic Phosphorus Compounds, vol 7, Edited Kosolapoff and Maier, p. 30, 1976.

*Primary Examiner*—Mindy Fleisher
*Assistant Examiner*—Terry A. McKelvey
*Attorney, Agent, or Firm*—Ron K. Levy; Steven M. Odre

[57] ABSTRACT

The present invention provides nuclease resistant 3'-carbon modified oligonucleotides that can be used in the field of nucleic acid therapeutics and diagnostics. The modified oligonucleotides of the present invention have at least one modified internucleotide linkage wherein the divalent oxygen moiety at the 3'-position of the internucleotide linkage is replaced by a tetravalent carbon moiety. The 3'-carbon modified internucleotide linkage is preferably a 3'-methylene or 3'-hydroxymethylene linkage. Also provided are a method and monomeric nucleoside and nucleotide intermediates for making the modified oligonucleotides of the present invention.

2 Claims, No Drawings

MODIFIED OLIGONUCLEOTIDES AND INTERMEDIATES USEFUL IN NUCLEIC ACID THERAPEUTICS

FIELD OF THE INVENTION

This invention relates to the field of therapeutics, and in particular the field of nucleic acid therapeutics.

BACKGROUND

Traditional approaches in drug development have focused on the use of therapeutic agents capable of interacting directly with proteins involved in disease states or other states of unhealth. Drugs borne of this tradition include, for example, synthetic hormones (to simulate the function of protein-based hormones desirably present in the body), antibiotics (which attack foreign proteins, namely microorganisms) and vitamins (which provide the building blocks required by certain proteins to perform their ordinary function in the body), in addition to many others. More recently, therapeutic agents in the form of oligonucleotides have been designed to indirectly regulate, control, or otherwise impact protein function by altering at the genetic level the blueprint or machinery that controls synthesis of all proteins. Because each gene contains the information necessary to produce many copies of a particular protein, each of these nucleic acid therapeutic agents can affect a greater number of protein molecules through its indirect interaction than can a traditional macromolecular drug that relies on direct interaction with the targeted protein.

Nucleic acid therapeutic compounds may act in a number of different ways, but will most commonly fall into either one of two categories. The first category includes oligonucleotides that simulate or potentiate in some way a desired genetic effect. The activity stimulated by this type of nucleic acid therapeutic compound is commonly referred to as "gene therapy". The second category of nucleic acid therapeutic compounds includes inhibitory oligonucleotides wherein the nucleic acid therapeutic compound inhibits the production of undesired proteins. Antisense oligonucleotides form a subclass of inhibitory nucleic acid therapeutic compounds, although compounds commonly assigned to this subclass may not always act in a true "antisense" manner. In addition to these two categories of therapeutic oligonucleotides, it should also be noted that it is also possible for nucleic acid therapeutic compounds to interact directly with the target proteins in much the same way as traditional therapeutic drugs.

True antisense interactions involve the hybridization of complementary oligonucleotides (hence, the term "antisense") to their selected nucleic acid target (e.g., viral RNA or other undesired genetic messages) in a sequence specific manner such that the complex thus formed, either alone or in combination with other reagent(s) (e.g., enzymes, such as RNAse) can no longer function as a template for the translation of genetic information into proteins. Other inhibitory oligonucleotides have sequences that are not necessarily complementary to a target sequence, but, like antisense oligonucleotides, have the potential to interfere with the expression (e.g., replication and/or translation) of the undesired genetic material. An antisense oligonucleotide may be designed to interfere with the expression of foreign genes (e.g., viral genes, such as HIV) or with the aberrant expression of endogenous genes (e.g., a normal gene that is aberrantly expressed as a mutated oncogene). These undesired genetic messages are involved in many disease states, including viral infections and carcinomas. Inhibitory oligonucleotides raise the possibility of therapeutic arrest of a disease state at the early replication and expression stage, rather than attacking the resulting protein at a later stage of disease progression as in the manner of traditional drugs.

Oligonucleotides used in gene therapy are designed to provide an oligonucleotide, or synthetic gene, having a desired effect that is otherwise absent or impaired in a patient. Each gene normally present in a human body is responsible for the manufacture of a particular protein that contributes to either the structure or functioning of the body. If this gene is defective or absent, protein synthesis will be faulty or nonexistent, and a deformity or genetic disease will result. Incorporation of nucleic acid therapeutic compounds into the genetic material of a patient's cells can be accomplished through a vehicle, such as a retrovirus, thus enabling production of the needed protein.

Irrespective of whether nucleic acid therapeutic compounds are designed for gene therapy, antisense therapy, or any other situation where it is desired to affect proteins at a genetic or other level, the design of these synthetic oligonucleotides is a key to the level of success that can be achieved. Importantly, these oligonucleotides must ordinarily be modified in a manner that imparts nuclease resistance to the oligonucleotide such that they are capable of surviving in the presence of the various nucleases that are endogenous to a human or animal body. The same holds true for oligonucleotide probes employed in the analysis of serum samples, because the same exogenous nucleases present in the human body that can degrade unmodified therapeutic oligonucleotides are also present in human serum and can degrade unmodified oligonucleotide probes in these samples as well.

Specifically, unmodified (or "wild type") oligonucleotides are susceptible to nuclease degradation at both the 3'- and 5'-positions of the internucleotide bonds that link the individual nucleoside units together in the completed oligonucleotide. Consequently, attempts to impart nuclease resistance to therapeutic oligonucleotides have been directed to modification of this internucleotide linkage, with success having been achieved primarily with respect to modification of the "non-bridging" oxygen atoms in the naturally occurring phosphodiester linkage. (E.g., phosphorothioate-modified oligonucleotides having a single non-bridging oxygen substituted with a sulfur atom (U.S. Pat. No. 3,846,402) and phosphorodithioate-modified oligonucleotides having both non-bridging oxygen atoms substituted with sulfur atoms (U.S. Pat. No. 5,218,103). However, sulfur-containing oligonucleotides such as these are known to bind to proteins, resulting in a level of non-specific activity that may not be acceptable. Moreover, phosphorothioate-modified oligonucleotides are particularly susceptible to nuclease degradation at the 3'-position of the modified internucleotide bonds, especially by nucleases leaving a 5'-phosphate following cleavage of the internucleotide bond, due to the fact that only one of the "non-bridging" oxygen atoms in the phosphodiester bond is modified.

There are a number of currently available methods for oligonucleotide synthesis that can be employed to generate oligonucleotides having modified backbones. These methods involve either solution or solid-phase synthesis. The more traditional approach of solution-based synthesis requires relatively small amounts of mononucleotide synthon reagents and can provide significant quantities of the desired end-product. However, solution synthesis has its drawback in that it requires tedious isolation and purification of the intermediate product following each addition of a mononucleotide subunit. As a result, solution-based phosphotriester chemistry is not suitable for the practical synthesis of longer oligonucleotides (i.e., greater than 6 bases in length) required for use in nucleic acid therapeutics. In the case of solid-phase synthesis, the entire reaction sequence is carried out on a solid support with mononucleotide subunits being added sequentially to form a growing chain attached at one end to the polymeric support. Thus, the solid-phase method allows for easy separation of the reagents, with the only real drawback of this method being that it requires an excess of the mononucleotide synthon reagents (several times the amount required for solution synthesis) as well as other expensive reagents.

It would be desirable to have a non-sulfur-containing modified oligonucleotide of a length that would be suitable for use as a nucleic acid therapeutic compound or as a diagnostic probe and would have a sufficient number of modified linkages to impart nuclease resistance to the modified oligonucleotide. It would be further desirable to have a polymer-supported method for synthesis of such a non-sulfur-containing modified oligonucleotide. One non-sulfur-containing modification involves substitution of a P—C bond in place of the P—O linkage at the 3'-position of an unmodified phosphodiester bond to yield a 3'-carbon modified internucleotide linkage. Monomeric 3'methylene phosphonate nucleotides necessary as intermediates for solution-based preparation of this modified phosphodiester bond have been prepared using solution chemistry. See, for example, Albrecht et al., *Tetrahedron*, 40, 79–85 (1984); Albrecht et al., *J. Amer. Chem. Soc.*, 92, 5511–5513 (1970); Morr et al., *GBF Monogr. Ser., Chem. Syn. Mol. Biol.*, 8, 107–113 (1987).

Traditional phosphodiester methods of solution phase synthesis have resulted in the incorporation of these monomeric modified oligonucleotide subunits into fully modified ribonucleotide 3'-methylene phosphonate dimers and trimers. Jones et al., *J. Amer. Chem. Soc.*, 92, 5510–5511 (1970, analog incorporated into dimer); Mazur et al., *Tetrahedron*, 40(20), 3949–3956 (1984) (analog incorporated into trimer). Furthermore, Morr et al., *GBF Monogr. Ser., Chem. Syn. Mol. Biol.*, supra., have reported the synthesis of a modified deoxyribonucleotide 3'-methylene phosphonate dimer from the same monomeric 3'-methylene phosphonate nucleosides with subsequent incorporation of the modified dimer (containing a single modified internucleotide linkage between the two monomeric subunits) into a longer oligonucleotide. Heinemann, et al., *Nucleic Acids Res.*, 19, 427 (1991). However, these procedures are far too laborious to be amenable to the large scale production of modified oligonucleotides.

The multiple 3'-carbon modifications necessary to impart nuclease resistance to an oligonucleotide have not been reported in deoxyoligonucleotides longer than a trimer, due to the inherent limitations of phosphotriester chemistry. Moreover, the solution-phase methodologies of the prior art cannot be applied to the more rapid and efficient polymer supported methodologies of oligonucleotide synthesis, because the phosphonate synthons used in the phosphotriester methods do not have sufficient coupling efficiencies to work effectively out of solution phase.

Therefore, it is an object of the present invention to provide monomeric oligonucleotide intermediates useful in the polymer-supported synthesis of 3'-carbon modified oligonucleotides.

It is a further object of the present invention to provide a polymer-supported method for synthesis of oligonucleotides having multiple 3'-carbon modifications.

It is a still further object of the present invention to provide oligonucleotides having at least one 3'-carbon modification useful in nucleic acid therapeutics and/or nucleic acid diagnostics.

SUMMARY OF THE INVENTION

The present invention provides nuclease resistant 3'-carbon modified oligonucleotides that can be used in the field of nucleic acid therapeutics and diagnostics. The modified oligonucleotides of the present invention have at least one modified internucleotide linkage wherein the divalent oxygen moiety at the 3'-position of the internucleotide linkage is replaced by a tetravalent carbon moiety. Also provided are a method and intermediates for making the modified oligonucleotides of the present invention.

DETAILED DESCRIPTION OF THE INVENTION

The present invention provides nuclease resistant 3'-carbon modified oligonucleotides useful in nucleic acid therapeutics and diagnostics. According to the present invention, the divalent oxygen moiety at the 3'-position of one or more of the internucleotide linkages of the oligonucleotide is replaced by a tetravalent carbon moiety, thus creating two additional substituent groups at the 3'-position. Also contemplated by the present invention is a method for making these modified oligonucleotides. Novel monomeric nucleoside and nucleotide intermediates useful in making the 3'-carbon modified oligonucleotides are also contemplated within the scope of the present invention.

The 3'-carbon modified oligonucleotides of the present invention have at least one modified internucleotide linkage wherein a P—C bond is substituted for the P—O bond at the 3'-position of the naturally occurring phosphodiester linkage. Unlike the P—O bond at the 3'-position of a naturally occurring phosphodiester linkage, the P—C bond of the 3'-carbon modified linkage cannot be cleaved by nucleases under normal physiological conditions. This P—C bond is obtained by substituting a 3'-methylene (designated —CH$_2$—), 3'-hydroxymethylene (designated —CHOH—) or other modified carbon function (designated —CXY—) for the 3'-oxygen in the internucleotide phosphodiester bond.

In order to aid in the understanding of the present invention, the following terms, as used herein, have the definitions designated below.

"Oligonucleotide" refers to a polymer of at least two nucleoside units, wherein each of the individual nucleoside units is covalently linked to at least one other nucleoside unit through a single phosphorus moiety. In the case of naturally occurring oligonucleotides, the covalent linkage between nucleoside units is a phosphodiester bond. Nevertheless, the term "oligonucleotide" as used herein, includes oligonucleotides that are modified (as compared to naturally occurring oligonucleotides) with respect to any one or more of the following: (1) the phosphodiester bond between nucleoside units; (2) the individual nucleoside units themselves; and/or (3) the ribose, or sugar, moiety of the nucleoside units.

Unless otherwise specified, the term "base" or "nucleobase" refers to a purine or pyrimidine, such as adenine, guanine, cytosine, thymidine and uracil as well as modified forms of these bases, such as 5-methylcytosine and 5-propynyl pyrimidines.

"Nucleoside" refers to an individual monomeric nucleoside unit consisting of a base covalently bonded to the 1'-position of a 5-carbon sugar. The 5-carbon sugar will typically be a naturally occurring sugar such as deoxyribose, ribose or arabinose, but can be any 5-carbon sugar or modified form thereof, including but not limited to, 2'-fluoro-2'-deoxyribose or even carbocyclic sugars where a carbon function is substituted for the oxygen atom in the sugar ring (i.e., 6 carbon analog). Typically, the base will be linked to the sugar moiety at conventional positions, such as N9 of adenine, guanine and other purines or N1 of cytosine, thymine, uracil and other pyrimidines.

"Nucleotide" refers to a monomeric nucleoside unit further having a phosphorus moiety covalently bonded to the sugar moiety of the nucleoside at either the 3'- or 5'-position of the sugar.

A "modified internucleotide linkage" refers to a modification of the phosphodiester bond joining individual nucleoside units in naturally occurring oligonucleotides.

The term "modified oligonucleotide" specifically refers to an oligonucleotide having at least one modified internucleotide linkage.

The term "partially modified oligonucleotide" means a modified oligonucleotide wherein at least one but fewer than all internucleotide linkages are modified.

The term "fully modified oligonucleotide" means a modified oligonucleotide wherein all of the internucleotide linkages are modified.

The term "3'-carbon internucleotide linkage" or "3'-carbon linkage" or "3'-carbon modified linkage" means an internucleotide linkage wherein the divalent oxygen moiety at the 3'-position of a phosphodiester internucleotide linkage is replaced by a tetravalent carbon moiety.

The term "3'-methylene internucleotide linkage" or "3'-methylene linkage" or "3'-methylene modified linkage" means a 3'-carbon internucleotide linkage wherein the tetravalent carbon atom at the 3'-position of the 3'-carbon linkage is covalently bonded independently to two hydrogen atoms.

The term "3'-hydroxymethylene internucleotide linkage" or "3'-hydroxymethylene linkage" or "3'-hydroxymethylene modified linkage" means a 3'-hydroxymethylene internucleotide linkage wherein the tetravalent carbon atom at the 3'-position of the 3'-carbon linkage is covalently bonded independently to both a hydrogen atom and a hydroxyl group.

The term "3'-carbon modified oligonucleotide" refers to an oligonucleotide having at least one 3'-carbon linkage.

The term "3'-methylene modified oligonucleotide" refers to an oligonucleotide having at least one 3'-methylene linkage.

The term "3'-hydroxymethylene modified oligonucleotide" refers to an oligonucleotide having at least one 3'-hydroxymethylene linkage.

"Target sequence" refers to the nucleotide sequence to which an oligonucleotide or a modified oligonucleotide is designed to hybridize. In the case of inhibitory oligonucleotides, the "target sequence" may be, but is not necessarily limited to, a naturally occurring messenger RNA coding for a viral protein, cancer related protein or other proteins involved in disease states.

Specifically, the 3'-carbon modified oligonucleotides of the present invention have at least one 3'-carbon modified internucleotide linkage as shown below.

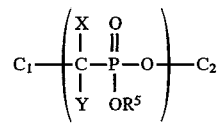

In this structure, C1 and C2 represent the 3'-position and 5'-position, respectively, of the nucleoside units which are joined together in the oligonucleotide through the 3'-carbon modified internucleotide linkage of the present invention.

This 3'-carbon modified internucleotide linkage can be more fully described with reference to the following structure, which shows the individual nucleoside units surrounding this particular linkage in greater detail:

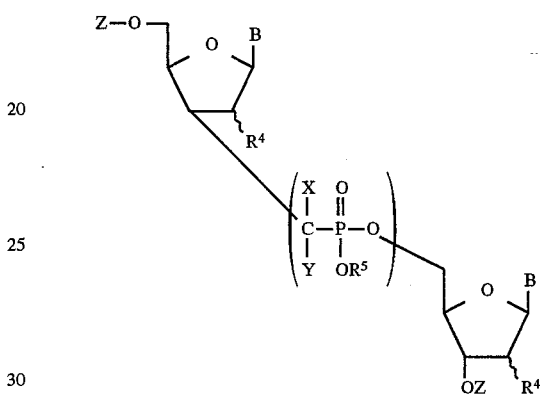

With reference to this oligonucleotide structure, B is a purine or pyrimidine base, typically adenine, guanine, cytosine or thymine (in the case of DNA) or uracil (in the case of RNA). Z is either a hydrogen (—H—) atom, where B is a terminal base of the oligonucleotide, or the phosphorus atom in the next internucleotide linkage of the oligonucleotide. $R^4$ is typically a hydrogen (—H—) atom (in the case of DNA) or a hydroxyl (—OH—) moiety (in the case of RNA, or in the case of an oligonucleotide having arabinose units in the backbone), but can be other atoms or moieties, such as fluorine (—F—) where other 5-carbon sugars are used in the backbone of the oligonucleotide.

$R^5$ represents a suitable counterion to the negatively charged, single-bonded oxygen atom in the internucleotide linkage. The preferred $R^5$ function in the 3'-carbon linkage will vary according to the particular application selected for use of the 3'-carbon modified oligonucleotides of the present invention and will be apparent to one of ordinary skill in the art following the teachings presented herein. For example, it will ordinarily be preferred that $R^5$ be a suitable counterions such as sodium, ammonium or alkylammonium, as these types of moieties tend to be the least disruptive to the natural structure of the oligonucleotide and is the most common counterion in wild type oligonucleotides as they exist in their salt form. However, during the chemical synthesis of oligonucleotides, $R^5$ can also be a suitable protecting group for the internucleotide linkage during the time it is subjected to relatively harsh chemical conditions.

The 3'-function, designated —CXY—, is a carbon function wherein X and Y are combinations of monovalent ligands that are generally designed to either: (1) cause minimal disruption of the structure of the internucleotide linkage; or, in some cases, (2) directly or indirectly (i.e., through derivatization) provide a label or other means for identifying or targeting the modified oligonucleotide. In the first instance, the —CXY— function of the 3'-modified linkage must be sufficiently small to enable the resulting 3'-carbon modified oligonucleotides to efficiently mimic naturally occurring nucleic acids, such as in their ability to hybridize strongly to their intended target. In this regard, preferred X and Y moieties include hydrogen (—H—) and fluorine (—F—) atoms and hydroxyl (—OH—) groups. Again, it may be preferred that both the X and Y moieties are hydrogen atoms (i.e., the 3'-carbon linkage is a 3'-methylene linkage) for the reason that hydrogen atoms can be expected to cause the least amount of disruption to the natural structure of the oligonucleotide.

However, in some cases, such as where recognition by RNAse H of a nucleic acid duplex containing the 3'-carbon modification is required, it may be desirable to incorporate a hydrophilic function, such as a hydroxyl (—OH—) group or fluorine (—F—) atom, on the 3'-carbon of the 3'-modified internucleotide linkage to provide a more effective substitution for the electronegative 3'-oxygen of naturally occurring internucleotide phosphodiester bonds. This is because modifications imparting hydrophilic character to the 3'-carbon (—CXY—) function would be expected to be more effective mimics of wild type oligonucleotides than more hydrophobic modifications, such as the two hydrogen atoms in a 3'-methylene (—CH$_2$—) modification. Thus, a preferred 3'-carbon modification also includes 3'-hydroxymethylene linkages where one of X or Y is a hydroxyl group. In this case, oligonucleotides containing multiple modified linkages can be expected to exhibit more effective hydration around the internucleotide linkage, allowing for a similar solution structure for these nucleic acid analogs relative to their naturally occurring counterparts.

During the chemical synthesis of oligonucleotides, efficiencies of the coupling reactions for each nucleoside unit that is added to the growing oligonucleotide greatly affect the overall efficiency of the reaction. For example, the theoretical yield for an 18-mer synthesized by the sequential addition of bases with a 95% efficiency for each coupling reaction is only 42%. The theoretical yield for the same 18-mer derived from sequential coupling reactions with 90% efficiency is a mere 17%. Even a 6-mer made using coupling reactions having 95% efficiency will only have a theoretical yield of 74%. Because separation of the growing oligonucleotide product from the background material following each coupling reaction is so laborious, time-consuming, and inefficient in the case of solution-based synthesis, these older methods of oligonucleotide synthesis cannot be effectively employed to generate modified oligonucleotides of the lengths generally required for diagnostic and therapeutic purposes. Moreover, the time consuming nature of solution-based synthesis adds significantly to the cost of the end product, making this synthetic method unfeasible for commercial production of oligonucleotides. The one exception, of course, is the case of a shorter oligonucleotide, most typically a dimer, that might be designed to interact directly with a protein. The time consuming nature of solution-based synthesis would not be a critical factor in making these shorter oligonucleotides.

The present invention further provides a rapid and efficient polymer-supported method for making oligonucleotides containing the 3'-carbon modified linkage described above. This rapid, automated method can be adapted to make 3'-carbon modified oligonucleotides of lengths comparable to those of unmodified oligonucleotides made by traditional polymer-supported techniques. This is important, because oligonucleotides of approximately 10–12 bases or longer are typically required for use as sequence specific probes for simple genomes such as E. coli. The upper limit of approximately 60 nucleotide bases is established for isothermal processes, because the melting temperatures ($T_m$) of longer oligonucleotide products converge upon the same value at or about this point. Antisense oligonucleotides, on the other hand, must be effective at physiological temperatures, and are typically about 15 to 25 nucleotides long. Generally, longer antisense oligonucleotides within this range are desirable, because they have a lower probability of occurring by chance in large genomes. For example, a 17-mer oligonucleotide should be unique to a mammalian genome. On the other hand, if an antisense oligonucleotide is too long (i.e., substantially longer than 25 nucleotides), it may hybridize nonspecifically to other non-target sequences. This type of nonspecific hybridization is unavoidable, because the physiological body temperature of a patient cannot be adjusted to increase stringency.

The method of the present invention requires the synthesis of a number of nucleoside intermediates en route to obtaining the desired 3'-carbon modified oligonucleotide end product. The key monomeric intermediates include nucleoside substrates, 3'-alkenyl nucleosides, 3'-aldehyde nucleosides and nucleotide synthons. Briefly, an aldehyde nucleoside is coupled to an aldehyde protected nucleotide synthon to form the 3'-carbon modified internucleotide linkage in the final coupling step of polymer-supported synthesis. A second synthon, namely a hydroxy protected nucleotide synthon, is also provided. This second synthon can be used to generate the 3'-carbon modified linkage in solution or to provide an unmodified 3'-position during polymer-supported synthesis. In these structures, which are depicted below, the nucleoside and nucleotide intermediates of the present invention are shown as deoxyribonucleosides and deoxyribonucleotides, although it is understood and appreciated that nucleosides and nucleotides containing other sugars, such as ribose, can also be made as intermediates to a modified oligonucleotide without departing from the teachings herein.

Ordinarily, it will be preferred to use commercially available nucleosides as the starting materials in the multi-step synthetic procedure of the present invention. It is preferred to initiate synthesis through formation of a nucleoside substrate by first protecting the 5'-position of the ribose or deoxyribose ring of the commercially available nucleoside unit and then derivatizing the 3'-position of the ring to form a suitable reactive group, such as a phenylthionocarbonate, to generate the nucleoside substrate. A deoxyribonucleoside substrate is shown below, wherein B is the base, R is a protecting group at the 5'-position and $R^1$ is a reactive group at the 3'-position of the nucleoside.

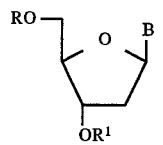

Nucleoside Substrate

Examples are provided in Table I, based on the chemical formula for the nucleoside substrate shown above, to demonstrate the sequence of steps for preparing a nucleoside substrate from the commercially available nucleosides thymidine ("T", a pyrimidine, compounds 1–3) and $N^6$-benzoyl-2'-deoxyadenosine ("$A^{Bz}$", a base protected purine, compounds 4–6).

TABLE I

| Compound | R | Base | R¹ |
| --- | --- | --- | --- |
| 1 | H | T | H |
| 2 | tBuMe$_2$Si | T | H |
| 3 | tBuMe$_2$Si | T | C(S)OPh |
| 4 | H | A$^{Bz}$ | H |
| 5 | tBuMe$_2$Si | A$^{Bz}$ | H |
| 6 | tBuMe$_2$Si | A$^{Bz}$ | C(S)OPh |

Compound 1 in Table I represents the underivatized form of the commercially available thymidine nucleoside reagent, while compound 4 represents the amino protected form of the commercially available 2'-deoxyadenosine reagent. Compounds 2 and 5, respectively, represent the same thymidine and N$^6$-benzoyl-2'-deoxyadenosine nucleoside reagents having been protected by derivatization of the 5'-hydroxyl group with a t-butyldimethylsilyl function prior to conversion of the 3'-hydroxyl group to the desired thionocarbonate (compounds 3 and 6). Protecting groups other than t-butyldimethylsilyl (e. g., dihydropyranosyl) can also be used to protect the 5'-hydroxyl group of the sugar moiety of the individual nucleoside units. The preferred protecting group will be apparent to one of ordinary skill in the art, taking into consideration factors such as the particular nucleoside sought to be derivatized and compatibility with other chemical methods, as well as other practical and commercial considerations.

The second key intermediate is a nucleoside analog having a double-bonded carbon function at the 3'-position of the sugar ring, referred to as a 3'-alkenyl nucleoside. This second intermediate is prepared from the nucleoside substrate described above. Specifically, these 3'-alkenyl nucleoside intermediates may be prepared from the corresponding thionocarbonates, such as compounds 3 and 6 in Table I. The 3'-alkenyl nucleosides have the general formula shown below.

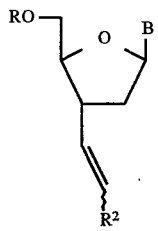

3'-Alkenyl Nucleoside

An alkylation reaction is required to generate the desired 3'-carbon derivatized nucleosides from the appropriate nucleoside substrate (e.g., from thionocarbonates). Typically, a cyano radical (.CN) alkylating reagent has been used to achieve alkylation in nucleoside chemistry. However, depending upon the conditions of the reaction and the nucleoside substrate being used, this type of alkylating reagent can generate optically impure racemic mixtures of the resulting 3'-carbon derivatized nucleosides. Racemic mixtures are not useful in generating oligonucleotides, because the wrong stereochemistry at the 3'-carbon bond will result in an incorrect internucleotide bond, thus preventing the appropriate helical structure required for biological activity of the oligonucleotide. However, it has surprisingly been found that an ethylene type tin-containing alkylating reagent having the general carbon-carbon double-bonded formula shown below can be used to generate an optically pure 3'-alkenyl nucleoside from a nucleoside substrate.

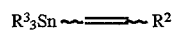

Ethylene Type Tin-Containing Alkylating Reagent

R$^2$ and R$^3$ of the alkylating reagent can be any organic group that does not interfere with the reactivity of the alkylating reagent or the stereochemistry of the reaction product. However, it is preferred that R$^2$ is an ethyl carboxylate group (CO$_2$Et) and R$^3$ is a butyl group, as set forth for the preferred tributyl tin ethyl acrylate in Table II, below. It is further preferred that the alkylating reagent be the cis form.

TABLE II

| Compound | R$^3$ | R$^2$ | Regioochemistry |
| --- | --- | --- | --- |
| 7 | Bu | CO$_2$Et | cis |
| 8 | Bu | CO$_2$Et | trans |

It is believed that the tin moiety of the alkylating reagent is capable of promoting radical chemistry. Because the tin alkylating reagent is bulkier than prior art cyano radical alkylating reagents, it is believed that the tin alkylating reagent takes advantage of steric hindrance to force all substitution to take place from one side of the ribose, or deoxyribose (or other sugar), ring of the nucleoside, thus creating an optically pure intermediate. In other words, the newly formed carbon-carbon bond at the 3'-position of the resulting 3'-alkenyl nucleoside will be entirely on one face of the ribose or deoxyribose ring.

Examples are provided in Table III to demonstrate the resulting 3'-alkenyl nucleosides generated from contacting the appropriate nucleoside substrate with the preferred cis t-butyl tin ethyl acrylate alkylating reagent, described above.

TABLE III

| Compound | R | Base | R$^2$ |
| --- | --- | --- | --- |
| 9 | tBuMe$_2$Si | T | CO$_2$Et |
| 10 | tBuMe$_2$Si | A$^{Bz}$ | CO$_2$Et |

Tin alkylating reagents of this type can be derived from modifications to procedures described for non-nucleotide synthesis, as described by Baldwin, et al., *J. Chem. Soc. Chem. Comm.*, 133–134 (1984) and Baldwin, et al., *J. Chem. Soc. Chem. Comm.*, 682–684 (1985), and these procedures can be adapted to nucleoside chemistry, as taught herein. In addition, it may be possible to adapt still other derivatives of this general structure that have been reported to be effective vinyl transfer groups. Crisp and Flynn, *Tetrahedron Letters*, 31, 1347–1350 (1990); Flynn, et al., *Nucleosides and Nucleotides*, 10, 763–779 (1991).

Compounds such as 9 and 10, shown in Table III, are suitable intermediates for the synthesis of modified oligonucleotides, because they may be converted effectively to the third key intermediate, namely nucleoside 3'-aldehyde derivatives and equivalents having the chemical formula shown below and exemplified in Table IV.

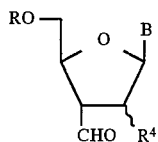

3'-Aldehyde Nucleoside

TABLE IV

| Compound | R | B | R⁴ |
|---|---|---|---|
| 11 | tBuMe₂Si | T | H |

These nucleoside aldehydes serve as direct intermediates, or substrates, for the synthesis of the 3'-carbon modified oligonucleotides of the present invention. The basic reaction for generating these 3'-carbon modified oligonucleotides is through a novel coupling reaction of the 3'-aldehyde nucleoside intermediate described above with coupling reagents having the general formula shown below in the presence of a basic catalyst.

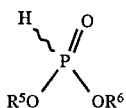

Coupling Reagent

In the case of oligonucleotide synthesis, $R^5$ is a protecting group and $R^6$ will ordinarily be a nucleotide component. In other words, the coupling reagent will be a nucleotide synthon as more fully described, infra. In those situations where $R^6$ is not a nucleotide component, $R^6$ will typically be a moiety useful in end-modification of an oligonucleotide.

Compounds 12, 13 and 14, shown in Table V, below, are specific examples of the coupling reagent used to incorporate the 3'-aldehyde nucleoside precursors into oligonucleotides. In this table, compound 12 is the commercially available dimethyl phosphite. Compounds 13 and 14 are 3'-hydroxy protected nucleotide synthons.

TABLE V

| Compound | R⁵ | R⁶ |
|---|---|---|
| 12 | Me | Me |
| 13 | Me | 3'-O-tBuMe₂SiT |
| 14 | Me | 3'-O-DMTrT |

Reaction of the coupling reagent with 3'-aldehyde nucleoside intermediates results in the formation of a modified nucleotide having the general formula shown below.

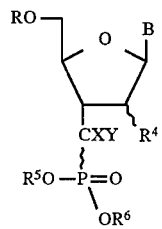

Modified Nucleotide

Table VI, below, demonstrates the modified nucleotides (compound 15) generated from tert-butyldimethylsilyl-protected thymidine 3'-aldehyde deoxyribonucleoside and coupling reagent 13.

TABLE VI

| Compound | R | CXY | B | R⁴ | R⁵ | R⁶ |
|---|---|---|---|---|---|---|
| 15 | tBuMe₂Si | X=OH, Y=H X=H, Y=OH | T | H | Me | 3'-O-tBuMe₂SiT |

The coupling reaction between the 3'-aldehyde nucleoside intermediate and 3'-hydroxy protected nucleotide synthons (e.g., coupling reagents 13 and 14 described above) is directly applicable for the solution-based synthesis of shorter oligonucleotides containing the 3'-carbon modified linkage of the present invention. Additionally, dialkyl phosphites, such as dimethyl phosphite (compound 12), can be coupled to the 3'-aldehyde nucleoside intermediate to generate nucleoside 3'-monophosphonates and dinucleoside 3'-monophosphonates.

However, for polymer supported synthesis of consecutive 3'-carbon modified internucleotide linkages, a 3'-aldehyde protected nucleotide synthon is required. This 3'-aldehyde protected nucleotide synthon is obtained by first protecting the aldehyde function of a 3'-aldehyde nucleoside with a protecting group that can be cleaved using relatively mild conditions, similar to cleavage of the dimethoxytrityl group in conventional oligonucleotide synthesis with trichloroacetic acid. Examples of this type of protecting group include the dithioacetal function and the N,N-diphenylimidazolidine function shown below.

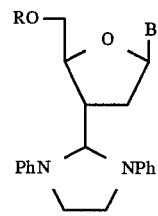

N,N-Diphenylimidazolidino Aldehyde Protected Nucleoside/Nucleotide

Other protecting groups suitable for protection of the aldehyde function of the 3'-aldehyde nucleoside will be apparent to those skilled in the art following the teachings of the present invention and include acetals, oxathiolanes and other recognized aldehyde protecting groups. Table VII, below, demonstrates variations of the N,N-diphenylimidazolidino aldehyde protected nucleoside.

TABLE VII

| Compound | R | B |
|---|---|---|
| 16 | tBuMe$_2$Si | T |
| 17 | H | T |
| 18 | HP(O)OMe | T |

Compounds 16 and 18 have additional groups (R) at the 5'-position. In the case of the aldehyde protected nucleoside of compound 16, deprotection of the 5'-position yields a free 5'-hydroxyl (compound 17) that can be further derivatized to a nucleoside alkyl phosphite (compound 18). This aldehyde protected nucleotide synthon can be used in the synthetic cycle for stepwise construction of 3'-carbon modified internucleotide linkages on a solid support.

Because the active phosphorus moiety in the 3'-aldehyde protected nucleotide synthon is attached to the 5'-position, polymer-supported synthesis of the modified oligonucleotide must proceed in a 5'→3'-direction, in contrast to conventional synthetic methods for the preparation of unmodified oligonucleotides. Although the unconventional 5'→3 direction of synthesis is known in the context of polymer-supported synthesis of unmodified oligonucleotides, synthesis in this direction is notoriously slow and, therefore, unfavored in a commercial environment. However, it has surprisingly been found that the aldehyde protected nucleotide synthons of the present invention enable rapid synthesis of 3'-carbon modified linkages in a 5'→3 direction.

Ordinarily, polymer-supported synthesis of oligonucleotides is initiated through a nucleoside that has been attached to a solid support as a starting point. The method of the present invention is no different in this regard. Specifically, nucleoside analogs containing the protected aldehyde function, but unprotected at the 5'-position, such as compound 17, are first attached to a suitable solid support through derivatization of the unprotected 5'-position according to established synthetic methods. A preferred solid support is controlled pore glass, but it will be appreciated that other solid supports are known in the art and will be suitable for synthesis according to the method of the present invention. Attachment of the first nucleoside to the solid support may be achieved using either the conventional succinyl or sarcosinyl linkers but is not limited to these reactions. The resulting suitably derivatized solid-support is then used to initiate the 5'→3' solid-phase synthesis of 3'-carbon modified oligonucleotides using conventional DNA/RNA synthesizers according to the following method.

Initially, the support is treated with acid which cleaves the aldehydic protecting group from the initial bound nucleoside. The free aldehyde of this attached nucleoside is then coupled with the a 3'-aldehyde protected nucleotide synthon, such as compound 18, to generate a hydroxymethylene-modified dimeric oligonucleotide on the solid support. Following several wash steps of the polymer-supported oligonucleotide, the support may again be treated with acid to regenerate the aldehyde function on what is now a growing modified oligonucleotide chain. Repetition of the coupling step elongates the oligonucleotide chain, one base at a time.

It is understood, however, that a number of different modifications may be made to this cycle according to the requirements of the particular oligonucleotide product to be synthesized. (E.g., synthesis of a partially modified oligonucleotide). These modifications are summarized below.

In conventional oligonucleotide synthesis, a "capping" step is necessary to avoid the further undesired coupling of failure sequences. For the synthetic method of the present invention, capping of the resin from the unwanted side-reaction of failure sequences may be effected using dimethyl phosphite (compound 12), which will terminate the growing chain of failed sequences.

The coupling reaction described herein is not limited to the coupling of 3'-aldehyde protected nucleotide synthons, such as compound 18. For example, a 3'-hydroxy protected nucleoside, such as compound 14, can also be coupled as the terminal step in a series of coupling reactions to leave a protected 3'-hydroxyl at the 3'-end of an oligonucleotide which, among other things, would tend to facilitate later purification of the oligonucleotide by high performance liquid chromatography (HPLC). Alternatively, compound 12 can also be coupled to the 3'-terminus. Likewise, other phosphite synthons can be attached to the 3'-terminus of the oligonucleotide. For example, the $R^6$ moiety of the coupling reagent shown in Table V can be, but is not limited to, such molecules as 3'-dideoxynucleosides or cholesterol or some fluorescent molecule like fluorescein or any desirable molecule compatible with this chemistry.

The coupling reaction of the present invention generates a free hydroxyl group on the 3'-carbon of the modified oligonucleotide. Thus, where 3'-hydroxymethylene linkages are desired, no further modification of the 3'-carbon is necessary. However, where other 3'-carbon modified linkages are desired, the hydroxyl function may be modified, either during or after synthesis of the oligonucleotide. For example, the hydroxyl group may be replaced with a hydrogen atom (in the case of 3'-methylene linkages) or a fluorine atom or other atom or group. If it is desired to have the modified oligonucleotide contain exclusively 3'-modified linkages (i.e., a fully 3'-carbon modified oligonucleotide), substitution of the free hydroxyl groups may be performed in a single step following construction of the desired oligonucleotide sequence. However, if different internucleotide linkages, such as unmodified (phosphodiester) linkages, are to be incorporated into a partially modified oligonucleotide product, substitution of the free hydroxyl group on the 3'-carbon modified linkages must be performed during the synthetic cycle following the construction of each individual 3'-carbon modified linkage.

The synthetic method of the present invention is compatible with current state-of-the-art methods for automated polymer-supported synthesis of oligonucleotides. Thus, the synthesis of a partially modified oligonucleotide, consisting of 3'-carbon modified linkages and unmodified (phosphodiester) linkages, can readily be achieved, provided the phosphodiester synthesis is carried out in the same unconventional 5'→3' direction for the phosphodiester linkages as is employed for incorporation of 3'-carbon modified nucleosides. For example, assuming phosphonate synthesis is first initiated as described above for the incorporation of 3'-carbon modified linkages, the desired number of 3'-carbon modified linkages are first synthesized, then the last 3'-aldehyde generated in the chain is coupled to a 5'-alkyl-3'-dimethoxytritylated-phosphite, such as compound 14, supra. Following this coupling reaction, the free hydroxymethylene phosphonate can be modified as described above or protected through "capping" with, for example, acetic anhydride. Final acid deprotection of the 3'-terminal dimethoxytrityl function yields a 3'-hydroxyl group that could be used to synthesize phosphodiester bonds through subsequent couplings with suitable 5'-phosphoramidites. If a return to phosphonate chemistry is desired, the terminal 3'-hydroxyl group can be reacted with a 5'-phosphoramidite synthon containing a protected aldehyde function such as compound 19.

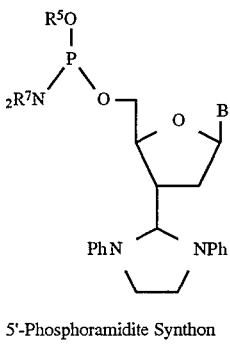

5'-Phosphoramidite Synthon

TABLE VIII

| Compound | R⁵ | R7 | B |
|---|---|---|---|
| 19 | $CH_3$ | $(CH_3)_2CH$ | T |

In this way oligonucleotide analogs can be constructed with at least one modified phosphonate linkage in any desired position. In a similar way, these chemistries can also be combined with other phosphoramidite-based technologies such as phosphorothioates, phosphorodithioates methylphosphonothioates and methylphosphonates.

It is also understood that the $R^5$ function is not necessarily restricted to the methyl group (Me, or $CH_3$). In this case any protecting group compatible with the chemistry may be used. Alternatively, other biologically desirable moieties can be attached to the modified oligonucleotide through the non-bridging atoms of the modified internucleotide linkage by synthesis of the appropriate phosphite/phosphoramidite (Compounds 12, 14, 18, 19; wherein $R^5$ is the group of interest).

Modified oligonucleotides can be deprotected according to established protocols for unmodified oligonucleotides. For example, where methyl protection is used at the phosphorus moiety, the protected oligonucleotide is first treated with thiophenol, or a recognized equivalent, to remove the methyl function. Following this reaction, the oligonucleotide is treated for the appropriate time with ammonia to cleave the oligonucleotide product from the solid support and to remove any base protecting groups, with purification being performed according to standard recognized methods such as HPLC or polyacrylamide gel electrophoresis.

The following examples are provided to aid in the understanding of the present invention, the true scope of which is set forth in the appended claims. It is understood that modifications can be made in the procedures set forth, without departing from the spirit of the invention.

Unless otherwise specified, solvents and reagents were obtained from commercial sources. 3'-O-tert-Butyldimethylsilylthymidine was prepared from reaction of commercially available 5'-O-(4,4'-dimethoxytrityl) thymidine with tert-butyldimethylsilyl chloride followed by removal of the trityl group with p-toluenesulfonic acid. 3'-O-(4,4'-Dimethoxytrityl)thymidine was prepared from reaction of 5'-O-tert-butyldimethylsilylthymidine (prepared as in Example 1) with 4,4'-dimethoxytrityl chloride followed by removal of the silyl group with tetrabutylammonium fluoride.

EXAMPLE 1

Synthesis of 5'-O-tert-Butyldimethsilylthymidine (Compound 2)

5'-O-tert-Butyldimethylsilylthymidine (Compound 2, Table I) was prepared by dissolving thymidine (25 g, 0.10 mole), 4-N,N-dimethylaminopyridine (3.15 g, 0.026 mole) and triethylamine (13.5 g, 18.6 ml, 0.13 mole) in 200 ml of dry N,N-dimethylformamide under a stream of argon. 19.4 g (0.13 mol) tert-butyldimethylchlorosilane was added to the dissolved mixture, with the entire mixture then being stirred for six hours before evaporation of the solvent. The resulting gum was dissolved in 30 ml ethyl acetate and the solution extracted with 10 ml saturated sodium bicarbonate solution, 30 ml water and 30 ml brine. Following drying of the organic layer, the residue was purified by flash chromatography using dichloromethane/ethanol (50/1) as eluent. Evaporation of the product-containing fractions yielded 31.5 g of the desired 5'-O-tert-butyldimethylsilylthymidine as a white foam (86% yield).

EXAMPLE 2

Synthesis of 5'-O-tert-Butyldimethylsilyl-3'-O-phenoxythiocarbonylthymidine (Compound 3)

5'-O-tert-Butyldimethylsilyl-3'-O-phenoxythiocarbonylthymidine (Compound 3, Table I) was prepared by dissolving 7.29 g (20.4 mmole) of the 5'-O-tert-Butyldimethylsilylthymidine from Example 1 in 100 ml dry dichloromethane and then adding 3.89 g (31.8 mmole) 4-N,N-dimethylaminopyridine and 3.58 g (20.74 mmole) phenylchlorothionoformate, followed by stirring at room temperature for 4 hours, at which time 10 ml water was added and the organic layer extracted with water. The organic layer was evaporated and the residue was purified by chromatography using 2% ethanol in dichloromethane as the eluent. Evaporation of the solvent from the product-containing fractions yielded 7.9 g of the protected nucleoside 5'-O-tert-butyldimethylsilyl-3'-O-phenoxythiocarbonylthymidine as a white foam (79% yield).

EXAMPLE 3

Synthesis of $N^6$-Benzoyl-5'-O-tert-butyldimethylsilyl-2'-deoxyadenosine (Compound 5)

$N^6$-Benzoyl-5'-O-tert-butyldimethylsilyl-2'-deoxyadenosine (Compound 5, Table I) was prepared by a procedure similar to that used to prepare the 5'-O-tertbutyldimethylsilylthymidine, as described in Example 1, except that $N^6$-benzoyl-2'-deoxyadenosine (10 g, 26.9 mmole), 4-N,N-dimethylaminopyridine (0.86 g, 7.0 mmole), triethylamine (3.6 g, 4.96 ml, 35.4 mmole) and tert-butyldimethylchlorosilane (5.33 g, 35.4 mmole) were dissolved in 100 ml dry N,N-dimethylformamide. The reaction was allowed to stir for 2 hours before being worked up as described in Example 1. Chromatography was performed using dichloromethane/ethanol (20/1) as eluent to yield 9.6 g $N^6$-benzoyl-5'-O-tert-butyldimethylsilyl-2'-deoxyadenosine as a white foam (73% yield).

EXAMPLE 4

Synthesis of $N^6$-Benzoyl-5'-O-tert-Butyldimethylsilyl-2'-deoxy-3'-O-phenoxythiocarbonyladenosine (Compound 6)

$N^6$-Benzoyl-5'-O-tert-butyldimethylsilyl-2'-deoxy-3'-O-phenoxythiocarbonyladenosine was prepared by a procedure similar to that used for 5'-O-tert- Butyldimethylsilyl-3'-O-phenoxythiocarbonylthymidine, as described in Example 2, except that 0.5 g (1.0 mmole) $N^6$-Benzoyl-5'-O-tert-butyldimethylsilyl-2'-deoxyadenosine from Example 3, 4-N, N-dimethylaminopyridine (0.26 g, 2.1 mmole) and phenylchlorothionoformate (0.24 g, 1.4 mmole) were dissolved in 20 ml dry dichloromethane. In this case, the reaction was stirred for 16 hours before work up in the usual way. Chromatography was performed using ethyl acetate in toluene as eluent to yield 0.39 g of the protected nucleoside $N^6$-benzoyl-5'-O-tert-butyldimethylsilyl-2'-deoxy-3'-O-phenoxythiocarbonyladenosine (Compound 6, 61% yield).

EXAMPLE 5

Synthesis of Ethyl-3-tributylstannyl-2-propenoate (Compounds 7 and 8)

Ethyl-3-tributylstannyl-2-propenoate (cis and trans forms, Compounds 7 and 8, Table II ) was prepared for use as an alkylating reagent by mixing ethyl propiolate (57.18 g, 0.58 mole), tributyl tin hydride (140 g, 129 ml, 0.48 mole) and azo-bis-isobutyronitrile (1 g, 0.007 mole) in a one liter round-bottomed flask. This mixture was freeze-pump-thaw degassed 3 times and then stirred in an oil bath at 80° C. for 4 hours (with great care being taken due to the potentially explosive nature of this reaction) after which time the reaction was removed from the oil bath and allowed to cool to room temperature. The cooled mixture was co-evaporated with 100 ml ethyl acetate and the resulting residue purified by column chromatography using hexane/dichloromethane (99/1) as eluent. Evaporation of the product-containing fractions yielded 73.5 g cis-ethyl-3-tributylstannyl-2-propenoate alkylating reagent (compound 7, 32% yield) and 66.8 g trans-ethyl-3-tributylstannyl-2-propenoate alkylating reagent (compound 8, 29% yield).

EXAMPLE 6

Synthesis of 5'-O-tert-Butyldimethylsily-3'-deoxy-3'-ethylacrylylthymidine (Compound 9)

5'-O-tert-Butyldimethylsilyl-3'-deoxy-3'-ethylacrylylthymidine was prepared by suspending 5'-O-tert-Butyldimethylsilyl-3'-O-phenoxythiocarbonylthymidine (1.4 g, 2.8 mole), hexamethylditin (0.46 g, 1.4 mmole) in cis-ethyl-3-tributylstannyl-2-propenoate (3.06 g, 7.9 mmole) in a 100 ml round-bottomed flask and then adding 0.14 g (1 mmole) azo-bis-isobutyronitrile to the solution. The mixture was freeze-pump-thaw degassed 3 times and then placed in an oil bath at 87° C. for 2 days. Approximately every 12 hours additional aliquots of 0.14 g azo-bis-isobutyronitrile (0.14 g) were added to the reaction mixture. Following the 2-day incubation period, the reaction was allowed to cool and the solvent was removed by evaporation. Chromatography of the residue with dichloromethane/ethanol (100/1) yielded, after evaporation of the appropriate fractions, 0.90 g 5'-O-tert-butyldimethylsilyl-3'-deoxy-3'-ethylacrylylthymidine (Compound 9, Table III) as a white foam (72% yield).

EXAMPLE 7

Synthesis of $N^6$-Benzoyl-5'-O-tert-butyldimethylsilyl-2',3'-dideoxy-3'-ethylacrylyladenosine (Compound 10)

$N^6$-Benzoyl-5'-O-tert-butyldimethylsilyl-2',3'-dideoxy-3'-ethylacrylyladenosine (Compound 10, Table III) was prepared by dissolving $N^6$-Benzoyl-5'-O-tert-butyldimethylsilyl-2'-deoxy-3'-O-phenoxythiocarbonyladenosine (50 mg, 0.08 mmole), cis-ethyl-3-tributylstannyl-2-propenoate (92 mg, 0.236 mmole) and hexamethylditin (13 mg, 0.04 mmole) in 2 ml toluene in a 40 ml Schlenk tube, and then adding 15 mg (0.11 mmole) azo-bis-isobutyronitrile to the mixture. The resulting mixture was freeze-pump-thaw degassed 3 times and then heated at 87° C. in an oil bath for 3 days. Approximately every 12 hours, fresh 15 mg azo-bisisobutyronitrile was added to the reaction. Following the 3-day incubation period, the reaction was cooled, the solvent evaporated, and the residue chromatographed with 1% ethanol in dichloromethane as eluent. A yield of 19 mg $N^6$-Benzoyl-5'-O-tert-butyldimethylsilyl-2',3'-dideoxy-3'-ethylacrylyladenosine was obtained as a white solid after evaporation of the appropriate fractions (42% yield).

EXAMPLE 8

Synthesis of 5'-O-tert-Butyldimethysilyl-3'-deoxy-3'-formylthymidine (Compound 11)

5'-O-tert-Butyldimethylsilyl-3'-deoxy-3'-formylthymidine (Compound 11, Table VII) was prepared by dissolving 5'-O-tert-Butyldimethylsilyl-3'-deoxy-3'-ethylacrylylthymidine (1 g, 2.3 mmole) and 4-methylmorpholine-N-oxide (0.52 g, 4.4 mmole) in a solution of 40 ml acetone and 4 ml water to give a clear pale yellow solution. Aqueous osmium tetroxide (11.2 ml, 0.050 g/ml, 2.2 mmole) was then added and the resulting pale yellow mixture stirred for 2 hours. After this time 1.17 g sodium periodate (5.47 mmole) was added to the reaction and stirring was continued for one more hour. The stirred mixture was then treated with 0.60 g sodium bisulfite and the reaction stirred for an additional hour. At this time the solvent was evaporated and the residue was redissolved in 30 ml ethyl acetate. The solution containing the redissolved residue was washed with water (3×20 ml) and then dried over anhydrous sodium sulfate. Evaporation of the solvent yielded 0.59 g 5'-O-tert-butyldimethylsilyl-3'-deoxy-3'-formylthymidine as a crude red foam that was generally used without further purification (71% yield).

EXAMPLE 9

Synthesis of 3'-O-tert-Butyldimethylsilythymidine-5'-O-methyl phosphite (Compound 13)

3'-O-tert-Butyldimethylsilylthymidine-5'-O-methyl phosphite (Compound 13, Table VIII) was prepared by first dissolving 3'-O-tert-butyldimethylsilylthymidine (1.3 g, 3.6 mmoles) in dry dichloromethane (15 ml) and triethylamine (2 ml) and to this solution was added N,N-diisopropylmethylphosphonamidic chloride (1.28 ml, 6.6 mmole). This mixture was stirred for 15 minutes before dilution into ethyl acetate (50 ml). The organic layer was washed with saturated sodium bicarbonate solution (50 ml) and water (50 ml) and the solvent was evaporated. This residue was redissolved in acetonitrile (15 ml) and to the solution was added water ( 0.53 ml, 29 mmole) and tetrazole solution (0.5M, 7.3 ml, 3.6 mmol). The reaction was stirred for 20 minutes before dilution of the mixture into dichloromethane (50 ml). This organic solution was washed with saturated sodium bicarbonate solution (50 ml), 10% sodium carbonate solution (50 ml) and brine (50 ml) and then dried over anhydrous sodium sulfate. Filtration and evaporation of the solvent afforded a gum that was purified on a chromatographic column. The column was first eluted with chloroform, then 2% ethanol in chloroform before elution of the product with 4% ethanol in chloroform. The product 3'-O-tert-butyldimethylsilylthymidine-5,'-O-methyl phosphite was obtained as a gum following evaporation of the solvent (1.1 g, 69%).

EXAMPLE 10

Synthesis of 3'-O-(4,4'-Dimethoxytrityl)thymidine-5'-O-methyl phosphite (Compound 14)

3'-O-(4,4'-Dimethoxytrityl)thymidine-5'-O-methyl phosphite (Compound 14, Table VIII) was prepared by twice coevaporating 3'-O-(4,4'-dimethoxytrityl)thymidine (0.85 g, 1.56 mmoles) with dry pyridine (20 ml) and dissolved in dry dichloromethane (8.5 ml) and triethylamine (0.68 ml). The solution was cooled to -78° C. using a dry ice/acetone bath and to this was added N,N-diisopropylmethylphosphonamidic chloride(0.49 ml, 2.52 mmoles). This mixture was stirred for 20 minutes before dilution into ethyl acetate (50 ml). The organic layer was washed with saturated sodium bicarbonate solution (50 ml) and water (50 ml) and the solvent was evaporated. This residue was redissolved in acetonitrile (15 ml) and then water (0.25 ml, 13.9 mmoles) and tetrazole solution (0.5M, 5.1 ml, 2.6 mmoles) added to the acetonitrile mixture. The reaction was stirred for 20 minutes before dilution of the mixture into dichloromethane (50 ml). This organic solution was washed with saturated sodium bicarbonate solution (50 ml), 10% sodium carbonate solution (50 ml) and brine (50 ml) and then dried over anhydrous sodium sulfate. Filtration and evaporation of the solvent afforded a gum that was dissolved in ethyl acetate (10 ml) for precipitation of the product into pentane (500 ml). The product 3'-O-(4,4'-dimethoxytrityl)thymidinyl-5'-O-methyl phosphite (Compound 14, Table VIII) was obtained as a white solid following filtration and drying overnight under vacuum with a yield of 0.75 g, or 77%.

EXAMPLE 11

Synthesis of 5'-O-tert-Butyldimethylsilyl-3'-deoxy-3'-methoxyphosphonylhydroxymethylthymidinyl-(3'→5')-3'-O-tert-butyldimethylsilylthymidine (Compound 15)

5'-O-tert-Butyldimethylsilyl-3'-deoxy-3'-methoxyphosphonylhydroxymethylthymidinyl-(3'→5')-3'-O-tert-butyldimethylsilylthymidine (Compound 15, Table IX) was prepared by first dissolving crude 5'-O-tert-butyldimethylsilyl-3'-deoxy-3'-formylthymidine (Compound 11, 0.78 g, 2.11 mmole, obtained from 1 g of Compound 9, according to Example 8) in dry pyridine (14 ml). This solution was mixed with a solution of 3'-O-tert-butyldimethylsilylthymidine-5'-O-methyl-H-phosphonate (1.91 g, 4.4 mmole) in benzene (20 ml) and to the mixture was added 1,8-diazabicyclo [5.4.0 ]undec-7-ene (DBU, 165 µl, 1.1 moles). The mixture was stirred for 30 minutes before evaporation of the solvent and chromatographic purification of the residue. Elution of the product was effected using 5% ethanol in dichloromethane as eluent to yield the desired product (Compound 15, 1.02 g, 56% calculated from Compound 9) as an off-white foam.

EXAMPLE 12

Synthesis of 5'-O-tert-Butyldimethylsilyl-3'-deoxy-3'(2-N,N-diphenylimidazolidino)-thymidine (Compound 16)

5'-O-tert-Butyldimethylsilyl-3'-deoxy-3'-(2-N,N-diphenylimidazolidino)-thymidine (Compound 16, Table X) was prepared by dissolving 5'-O-tert-butyldimethylsilyl-3'-deoxy-3'-formylthymidine (1.3 g, 3.5 mmole) in 30 ml benzene and then adding 1.5 g (7.0 mmole) 1,2-dianiliinoethane to the solution. The resulting mixture was stirred overnight at 60° C. At this time, 20 ml saturated aqueous sodium bicarbonate was added and the solution was extracted with ethyl acetate (3×30 ml). After drying over anhydrous sodium sulfate, the organic layer was evaporated and the residue was chromatographed with ethanol/triethylamine/dichloromethane (1/2/97) as eluent. A yield of 1.25 g 5'-O-tert-Butyldimethylsilyl-3'-deoxy-3'-(2-N,N-diphenylimidazolidino)-thymidine was obtained as a light brown solid following evaporation of the appropriate fractions (63% yield).

EXAMPLE 13

Synthesis of 3'-Deoxy-3'-(2-N,N-diphenylimidazolidino)-thymidine (Compound 17)

3'-Deoxy-3'-(2-N,N-diphenylimidazolidino)-thymidine (Compound 17, Table X) was prepared by dissolving 5'-O-tert-butyldimethylsilyl-3'-deoxy-3'-(2-N,N-diphenylimidazolidino)-thymidine (0.8 g, 1.4 mmole) in 50 ml THF, stirring, and then adding tetrabutylammonium fluoride (1M solution in THF, 8.3 ml, 8.3 mmol) to the stirred solution. The resulting mixture was stirred for 30 minutes. Triethylamine (2 ml) was added before evaporation of the solvent. The residue was purified by flash chromatography using ethanol/triethylamine/dichloromethane (2/2/96) as eluent. Product-containing fractions were evaporated and the residue was precipitated into pentane to yield 0.63 g 3'-deoxy-3'-(2-N,N-diphenylimidazolidino)-thymidine as a light brown solid (99% yield).

EXAMPLE 14

Synthesis of 3'-Deoxy-3'-(2-N,N-diphenylimidazolidino)-thymidine-5'-O-methyl phosphite (Compound 18)

Synthesis of 3'-deoxy-3'-(2-N,N-diphenylimidazolidino)-thymidine-5'-O-methyl phosphite (Compound 18, Table X) was prepared by twice coevaporating 3'-deoxy-3'-(2-N,N-diphenylimidazolidino)-thymidine (200 mg, 0.45 mmoles) with dry pyridine (20 ml) and dissolved in dry dichloromethane (5 ml) and triethylamine (0.17 ml). The solution was cooled to −78° C. using a dry ice/acetone bath and to this was added N,N-diisopropylmethylphosphonamidic chloride (0.14 ml, 0.72 mmoles). This mixture was stirred for 20 minutes when a further portion of N,N-diisopropylmethylphosphonamidic chloride (0.02 ml, 0.01 mmoles) was added. After a further 15 minutes the mixture was diluted into ethyl acetate (50 ml). The organic layer was washed with saturated sodium bicarbonate solution (50 ml) and water (50 ml), and the solvent then evaporated. This residue was redissolved in acetonitrile (5 ml) and then water (0.16 ml, 2.9 mmoles) and tetrazole solution (0.5M, 1.0 ml, 0.5 mmoles) added to the acetonitrile mixture. The reaction was stirred for 20 minutes before dilution of the mixture into dichloromethane (50 ml). This organic solution was washed with saturated sodium bicarbonate solution (50 ml), 10% sodium carbonate solution (50 ml) and brine (50 ml) and then dried over anhydrous sodium sulfate. Filtration and evaporation of the solvent afforded a gum that was dissolved in ethyl acetate (3 ml). Pentane (400 ml) was added to precipitate the product. The resulting supernatant was decanted and the solid was washed with pentane before drying overnight under vacuum to generate 180 mg of product, representing a 76% yield.

EXAMPLE 15

3'-Deoxy-3'- (2-N,N-diphenylimidazolidino)-thymidine-5'-N,N-diisopropyl-O-methyl phosphoramidite (Compound 19)

3'-Deoxy-3'-(2-N,N-diphenylimidazolidino)-thymidine-5'-N,N-diisopropyl-O-methyl phosphoramidite (Compound 19, Table 10) was prepared by twice coevaporating 3'-deoxy-3'-(2-N,N-diphenylimidazolidino)-thymidine (200 mg, 0.45 mmoles) with dry pyridine (20 ml) and then dissolving the resulting solid in dry dichloromethane (5 ml) and triethylamine (0.17 ml). To this solution at room temperature was added N,N-diisopropylmethylphosphonamidic chloride (0.12 ml, 0.62 mmoles). After 15 minutes the mixture was diluted into ethyl acetate (50 ml). This organic solution was washed with saturated sodium bicarbonate solution (50 ml), 10% sodium carbonate solution (50 ml) and brine (50 ml) and then dried over anhydrous sodium sulfate. Filtration and evaporation of the solvent afforded a gum that was dissolved in ethyl acetate (3 ml). Pentane (400 ml) was added to precipitate the product. The resulting supernatant was decanted and the solid was washed with pentane before drying overnight under vacuum (yield 160 mg, 59%).

EXAMPLE 16

Synthesis of Oligonucleotide Analogs

A. Attachment of 3'-deoxy-3'-(2-N,N-diphenylimidazolidinol)-nucleosides to solid supports Derivatized nucleosides are attached to an appropriate solid support via the 5'-hydroxyl such that analog synthesis may proceed in a 5'→3'- direction. For example:

3'-deoxy-3'-(2-N,N-diphenylimidazolidino)-thymidine (200 mg, 0.43 mmole) and 4-N,N-dimethylaminopyridine (78.5 mg, 0.65 mmole) were coevaporated with dry pyridine (2×20 ml). The residue obtained was dissolved in dry pyridine (20 ml) and to the solution was added succinic anhydride (34.4 mg, 0.34 mmole). This reaction mixture was allowed to stir overnight. After this time, the solvent was evaporated and the residue was coevaporated with toluene before dissolution into dichloromethane (50 ml). The organic layer was washed twice with water (20 ml) and dried over anhydrous sodium sulfate. Filtration yielded a clear solution that was concentrated to about 10 ml for precipitation of the product in hexane/ether (1/1, 50 ml). The product 3'-deoxy-3'-(2-N,N-diphenylimidazolidino)-thymidine-5'-O-succinate (195 mg, 80%) was isolated by filtration and used without further purification.

The succinylated nucleoside (240 mg, 0.43 mmole) was dissolved in a mixture of dry pyridine (5 ml) and dry dioxane (5 ml). To the solution was added 1,3-dicyclohexylcarbodiimide (177 mg, 0.86 mmole) and 4-nitrophenol (60 mg, 0.43 mmole) and the reaction mixture was stirred overnight. At this point the precipitate was filtered and the solvent was evaporated. The residue was twice coevaporated with toluene (10 ml) and the crude 3'-deoxy-3'-(2-N,N-diphenylimidazolidino)-thymidine-5'-O-succinate-(4-nitrophenyl) ester then used to derivatize controlled pore glass.

Long chain alkylamine derivatized controlled pore glass (89 μmole/g) was suspended in dry tetrahydrofuran (THF, 5 ml) and to this was added the crude 3'-deoxy-3'-(2-N,N-diphenylimidazolidino)-thymidine-5'-O-succinate-4-nitrophenyl ester as a solution in THF (3 ml) and triethylamine (2.3 ml). This mixture was shaken overnight and the derivatized support was isolated by filtration. The support was washed with N,N-dimethylformamide (3×10 ml), dioxane (3×10 ml), methanol (5×10 ml) and ether (3×10 ml).

Capping of the resin was effected through suspension of the controlled pore glass in dry pyridine and treatment with acetic anhydride (0.5 ml). This mixture was shaken for 30 minutes. The fully functionalized support was then filtered and washed with methanol (6×10 ml) and ether (3×10 ml) before drying.

B. Synthesis of Oligonucleotide Phosphonates

Synthesis of oligonucleotide analogs was performed using an Applied Biosystems 394 DNA/RNA synthesizer. Using this instrument, analogs containing either uniform or intermittent phosphonate functions may be synthesized using reagents described above.

C. Synthesis of a Fully Modified Oligonucleotide

In the simplest case solid support modified with 3'-deoxy-3'-(2-N,N-diphenylimidazolidino)-nucleoside is deblocked in the presence of acid to yield the 3'-formyl nucleoside attached to the resin. Following washing of the resin to remove the acid, coupling is achieved in the presence of 3'-modified-5'-phosphite such as compound 18 (0.1M in benzene) using DBU (53 mM in pyridine) as activator. Synthesis proceeds in a 5'→3' direction. Following additional wash steps, the cycle was be repeated using monomeric building blocks such as Compound 18 to generate the appropriate sequence. A 3'-O-dimethoxytritylated phosphite such as 14 (0.1M in benzene) was coupled as the final (3'-terminal) nucleotide in the sequence. For example, the automated steps required to synthesize six uniform hydroxymethylene phosphonate linkages with thymidine as the nucleobase (at approximately 0.5 μM scale) were as follows:

| Step | Reagent/Solvent | Time/min |
|---|---|---|
| 1 | 3% Trichloroacetic acid in dichloromethane | 3.0 |
| 2 | Dichloromethane | 0.3 |
| 3 | Pyridine/benzene (1/1) | 0.3 |
| 4 | Compound 18 (0.1M in benzene) plus DBU* (54 mM in pyridine) | 2.0 |
| 5 | Pyridine/benzene (1/1) | 0.3 |
| 6 | Dichloromethane | 0.3 |
| 7 | Steps 1–6 were repeated for each addition of Compound 18 (in this case four additional times) | |
| 8 | For the terminal nucleotide unit steps 1–6 | |

| Step | Reagent/Solvent | Time/min |
| --- | --- | --- |
| | were repeated with the exception that Compound 14 (0.1M in benzene) replaced Compound 18 in the coupling step (step 4). | |

A fully modified heptamer, designated T*T*T*T*T*T*T (* indicating the position of a 3'-hydroxymethylene modified internucleotide linkage), containing six consecutive 3'-hydroxymethylene phosphonate internucleotide bonds, was synthesized according to this procedure, resulting in a yield of 71% (31P NMR ($D_2O$); δ19–20 ppm). The modified oligonucleotide was purified by standard HPLC techniques (e.g., *Evaluating and Isolating Synthetic Oligonucleotides*, User Bulletin 13 (Applied Biosystems Inc. 1987) using trityl as a protecting group and then detritylated according to the procedure of Wiesler et al., *Synthesis and Purification of Phosphorodithioate DNA*, from *Protocols for Oligonucleotides and Analogs; Synthesis and Properties*, 191–206 (Ed. Agrawal, Humana Press 1993).

D. Synthesis of a Partially Modified Oligonucleotide

This example demonstrates the use of the chemistry used to generate the phosphonate linkage in conjunction with conventional methods of oligonucleotide chemistry such as phosphoramidite chemistry. An example is shown for the synthesis of a 14-mer oligothymidylate having a single 3'-hydroxymethylene modified internucleotide linkage between the second and third bases on the 5'-end of the oligonucleotide. However, as with the synthesis of a completely modified oligonucleotide, as demonstrated in Example 16C, synthesis proceeds from a 5'→3'- direction. In this example, commercially available 3'-dimethoxytritylated solid support was detritylated using standard machine protocols and coupled with 3'-deoxy-3'-(2-N,N-diphenylimidazolidino)-thymidine-5'-N,N-diisopropyl-O-methylphosphoramidite (Compound 19, 0.1M in acetonitrile) in the presence of tetrazole (0.5M in acetonitrile) for 5 minutes. Following coupling, standard capping and oxidation protocols are applied. After synthesis of this dinucleotide unit, protocols outlined in section 8 of the above cycle for uniform hydroxymethylene phosphonate were applied to generate a single hydroxymethylene phosphonate linkage with a terminal 3'-dimethoxytrityl function. At this point the solid support was treated with the machine capping solutions for 5 minutes. The remainder of the sequence is completed using commercially available 5'-O-cyanoethyl-N,N-diisopropylphosphoramidites (in this example of thymidine) using standard machine protocols for these phosphoramidites.

A 14-mer oligothymidylate containing one hydroxymethylene phosphonate linkage (18% yield: 31P NMR ($D_2O$); δ19–20 ppm hydroxymethylene phosphonate; 0 ppm phosphodiester).

E. Measurement of derivatized CPG loading capacity:

Loading of the modified deoxyribonucleoside was estimated by performing a single coupling cycle. In this case the resin was treated with trichloroacetic acid, washed with solvent and coupled with 3'-O-(4,4'-Dimethoxytrityl) thymidine-5'-O-methyl phosphite (Compound 14, 0.1M in benzene) in the presence of DBU (53 mM in pyridine). Quantitation of the dimethoxytrityl cation release upon treatment of the solid support with trichloroacetic acid in methylene chloride was then used to estimate the modified nucleosides loading to the CPG.

The trityl fraction was collected in a 10 ml volumetric flask and the bright orange trityl cation solution was diluted to 10 ml with 0.1M p-toluenesulfonic acid. 200 μl of this solution in 800 μl of 0.1M p-toluenesulfonic acid in acetonitrile gave an absorbance reading from which the loading capacity can be calculated as follows:

$$\text{Loading (}\mu\text{mole/g)} = \frac{A498 \times 1000 \times \text{(dilution factor)} \times V}{E \times \text{(amount of CPG in } g\text{)}}$$

where:

A498=absorbance at 498 nm of the solution

V=total volume of the stock solution

E=extinction coefficient of the dimethoxytrityl cation ($7 \times 10^4$ liter/mol).

In this way modified nucleoside loadings of 4–10 μmoles/g were obtained for the derivatized solid supports.

F. Deprotection of internucleotide phosphonate triesters and their cleavage from support To a 1 μmole synthesis of oligonucleotide CPG (argon dried) was added 1 ml of a 1M solution (in dimethylformamide) of disodium 2-carbamoyl-2-cyanoethylene-1,1-dithiolate. The deprotection was allowed to proceed overnight (16 hours) at room temperature. Upon completion, the CPG was washed three times with water, followed by three times with acetone. The CPG linked phosphodiester was then dried under argon and cleaved from the support by the addition of 2 ml 30% $NH_4OH$. Cleavage was complete after 3 hours at room temperature. Drying under vacuum afforded a residue that was quantifiable by dissolution in 1 ml water and measuring absorbance at 260 lambda.

Disodium 2-carbamoyl-2-cyanoethylene-1,1-dithiolate was prepared according to published procedures (Dahl, et al., *Acta Chemica*, 44, 639–641 (Scandinavica, 1990).

Sodium (4.6 g, 0.2 moles) was carefully dissolved in ethanol (125 ml). To this solution was added drop-wise a suspension of cyanoacetamide (16.8 g, 0.2 moles) in ethanol (50 ml). Carbon disulfide (12.2 ml, 0.2 moles) was then added to the resulting suspension and the mixture was allowed to stir for one hour. A further portion of sodium (4.6 g, 0.2 moles) was then added as a solution in ethanol (125 ml). Following the addition, the mixture was refrigerated overnight in order to allow the product to precipitate. The solid was filtered and then washed with ethanol. This crude material was redissolved in 80% aqueous methanol (100 ml) and to the solution was added ethanol (300 ml). The product was allowed to crystallize at 4° C. overnight before being collected by filtration (Yield 36.4 g, 70%).

EXAMPLE 17

Nuclease Resistance of Modified Oligonucleotides

This example demonstrates the nuclease resistance of the modified oligonucleotides of the present invention, as compared to unmodified (wild type) oligonucleotides, when contacted with a 3'-exonuclease and a 5'-exonuclease. The 3'-hydroxymethylene heptamer from Example 16C was used as a representative 3'-carbon modified oligonucleotide. A corresponding unmodified 7-mer oligonucleotide, identical in sequence but containing only unmodified phosphodiester bonds, was synthesized on an automated synthesizer according to standard polymer-supported synthetic techniques for use as a control in the following procedures.

The 3'-methylene modified oligonucleotide was analyzed for susceptibility to nuclease digestion according to two different methods. In the first method, both the modified oligonucleotide and the unmodified control were labeled with radioactive phosphorus ($^{32}$P) at their respective 5'-ends and then assessed for stability by first contacting the oligonucleotides with the 3'-exonuclease snake venom phosphodiesterase and then measuring the size of the resulting oligonucleotide product(s) using polyacrylamide gel electrophoresis (PAGE) according to standard techniques. In the second method, the modified oligonucleotide and its unmodified counterpart were analyzed for degradation in the presence of the 5'-exonuclease calf spleen phosphodiesterase by the nuclease via high performance liquid chromatography (HPLC).

A. Resistance to Snake Venom Phosphodiesterase

Both the modified oligonucleotide and its phosphodiester counterpart (control) were labeled using $\gamma$-$^{32}$P-ATP and polynucleotide kinase according to standard techniques known in the art. The excess $\gamma$-$^{32}$P-ATP was separated from the oligonucleotides by gel filtration through G-50 Sephadex®(Pharmacia).

The radioactive oligonucleotide solutions containing 3.4 pmol of oligonucleotide were treated with 0, $0.3\times10^{-5}$, $0.6\times10^{-5}$, $1.2\times10^{-5}$, $2.4\times10^{-5}$ and $4.8\times10^{-5}$ units of snake venom phosphodiesterase (Boehringer Mannheim, Germany), respectively, and the resulting solutions incubated at 37° C. for 30 minutes. Following incubation, an equal volume of 90% formamide containing bromophenol blue, xylene cyanol and 25 mM EDTA was added to each oligonucleotide solution and the mixtures heated at 90° C. for 5 minutes. The samples were then analyzed by separation on a 20% denaturing polyacrylamide gel.

With the exception of the 0 unit reaction, the phosphodiester (unmodified) oligonucleotide was degraded in all reactions. Degradation was complete in all the reactions using $1.2\times10^{-5}$ or higher units of enzyme. In contrast, no significant degradation of the modified (hydroxymethylene phosphonate) oligonucleotide was observed in any reaction.

B. Resistance to Calf Spleen Phosphodiesterase

One 250 μl unit of a suspension of the exonuclease calf spleen phosphodiesterase (Boehringer Mannheim) was added to each oligonucleotide solution of interest (0.5 $A_{260}$ units) and the solution made up to a total volume of 300 μl with tris-EDTA buffer (0.1M). After 30 minutes incubation at room temperature the reactions were analyzed by HPLC using 50 mM sodium phosphate, pH 6, as the aqueous phase with a gradient of 0–30% acetonitrile over 25 minutes. Products were identified by comparison to chromatographs of standard samples.

Under these conditions the phosphodiester (unmodified) oligonucleotide was 80% degraded by the enzyme while, for the modified oligonucleotide, approximately 16% of a cleavage product was observed.

What is claimed is:

1. A modified oligonucleotide of between 12 and 60 bases having at least three consecutive 3'-hydroxymethylene modified internucleotide linkages of the structure:

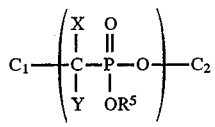

wherein, $R^5$ is a counterion, $C_1$ and $C_2$ represent the 3'-position and 5'-position, respectively, of the nucleoside units which are joined together in said oligonucleotide through said 3'-hydroxymethylene internucleotide linkages, and one of either X or Y is a hydroxyl (—OH—) group and the other of said X or Y is a hydrogen (—H—) atom.

2. A fully modified oligonucleotide of between 12 and 60 bases having only 3'-hydroxymethylene modified internucleotide linkages of the structure:

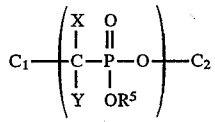

wherein, $R^5$ is a counterion, $C_1$ and $C_2$ represent the 3'-position and 5'-position, respectively, of the nucleotide units which are joined together in said oligonucleotide through said 3'-hydroxymethylene modified internucleotide linkages, and one of either X or Y is a hydroxyl (—OH—) group and the other of said X or Y is a hydrogen (—H—) atom.

* * * * *